United States Patent
Missbach

(10) Patent No.: US 6,642,239 B2
(45) Date of Patent: Nov. 4, 2003

(54) DIPEPTIDE NITRILE CATHEPSIN K INHIBITORS

(75) Inventor: Martin Missbach, Gipf-Oberfrick (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/778,302

(22) Filed: Feb. 7, 2001

(65) Prior Publication Data

US 2001/0016207 A1 Aug. 23, 2001

(30) Foreign Application Priority Data

Feb. 10, 2000 (GB) .............................. 0003111

(51) Int. Cl.$^7$ .................. C07D 295/14; A61K 31/451; A61P 19/10; A61P 19/02
(52) U.S. Cl. .................. 514/255.03; 514/331; 544/393; 546/230
(58) Field of Search ........................... 514/255.03, 331; 544/393; 546/230

(56) References Cited

U.S. PATENT DOCUMENTS

| | | | |
|---|---|---|---|
| 3,467,691 A | 9/1969 | Irikura et al. | |
| 3,697,577 A | 10/1972 | Irikura et al. | |
| 5,574,064 A | 11/1996 | Shibata et al. | |
| 5,780,498 A | 7/1998 | Saika et al. | |
| 6,353,017 B1 | 3/2002 | Altmann et al. | 514/428 |
| 6,455,502 B1 | 9/2002 | Bryant et al. | 514/19 |
| 6,476,026 B1 | 11/2002 | Bryant et al. | 514/235.8 |
| 2002/0086996 A1 | 7/2002 | Bryant et al. | 544/163 |

FOREIGN PATENT DOCUMENTS

| | | |
|---|---|---|
| BE | 662788 | 8/1965 |
| EP | 506 008 A1 | 9/1992 |
| EP | 547 699 A1 | 6/1993 |
| EP | 587 110 A2 | 3/1994 |
| EP | 611 756 A2 | 8/1994 |
| WO | WO 95 12611 | 5/1995 |
| WO | WO 96 20949 | 7/1995 |
| WO | WO 95 24382 | 9/1995 |
| WO | WO 96 33170 | 10/1996 |
| WO | WO 97/27200 | 7/1997 |
| WO | WO 98 01133 | 1/1998 |
| WO | WO 98/22433 | 5/1998 |
| WO | WO 99/24460 | 5/1999 |
| WO | WO 00/49007 | 8/2000 |
| WO | WO 00/49008 | 8/2000 |
| WO | WO 00/51998 | 9/2000 |
| WO | WO 00/55125 | 9/2000 |
| WO | WO 00/55126 | 9/2000 |
| WO | WO 00/55126 A2 * | 9/2000 |

OTHER PUBLICATIONS

Lowe et al., Biochem.J., vol. 124, No. 1, pp. 107–115 (1971).
Buttle et al., Biochem. J., vol. 261, No. 2, pp. 469–476 (1989).
Baker et al., Biochimica Biophysica Acta, vol. 616, pp. 30–34 (1980).
Liu et al., Biochemica Biophysica Acta, vol. 1250, pp. 43–48 (1995).
Stevenson et al., Biotechnology & Bioengineering, vol. 37, pp. 519–527 (1991).
Grzegorzewska et al., Bull.Acad.Pol.Sci., Ser.Sci.Chim., vol. 22, No. 8, pp. 679–683 (1974).
Varughese et al., Can.J.Chem., vol. 64, No. 8, pp. 1668–1673 (1986).
Gour–Salin et al.,Can.J.Chem., vol. 69, No. 8, pp. 1288–1297 (1991).
Suzue et al., Chem.Pharm.Bull., vol. 16, No. 8, pp. 1417–1432 (1968).
Gour–Salin et al.,Enzyme Microb.Technol., vol. 13, pp. 408–411 (1991).
Von Heinz Moser et al., Helvetica Chimica Acta, vol. 69, pp. 1224–1262 (1986).
Lipshutz et al., Israel Jour. of Chemistry, vol. 27, pp. 49–55 (1986).
Carey et al., Journal of Biological Chemistry, vol. 259, No. 23, pp. 14357–14360 (1984).
Elmore et al., J.Chem.Soc.Perkin Trans., vol. 1, pp. 1051–1055 (1988).
Campbell et al., J.Am.Chem.Soc., vol. 104, pp. 5221–5226 (1982).
Lipshutz et al., J.Am.Chem.Soc., vol. 105, pp. 7703–7713 (1983).
Moon et al., J.Am.Chem.Soc., vol. 108, pp. 1350–1351 (1986).

(List continued on next page.)

Primary Examiner—Mukund J. Shah
Assistant Examiner—Thomas McKenzie
(74) Attorney, Agent, or Firm—Norbert Gruenfeld

(57) ABSTRACT

Dipeptide nitrile Cathepsin K inhibitors of formula I, and pharmaceutically acceptable salts or esters thereof:

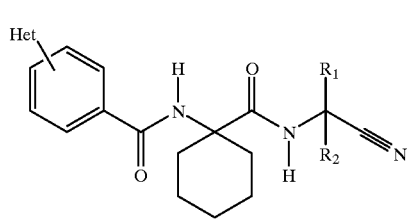

In which
R$_1$ and R$_2$ are independently H or C$_1$–C$_7$ lower alkyl, or R$_1$ and R$_2$ together with the carbon atom to which they are attached form a C$_3$–C$_8$ cycloalkyl ring, and
Het is an optionally substituted nitrogen-containing heterocyclic substituent, are provided, useful e.g. for therapeutic or prophylactic treatment of a disease or medical condition in which cathepsin K is implicated.

11 Claims, No Drawings

OTHER PUBLICATIONS

Katritzky et al., Organic Prep.Proced.Int., vol. 24, No. 2, pp. 121–126 (1992).
Eugen Vargha, Stud.Univ.Babes–Bolyai.Ser.Chem., vol. 13, No. 2, pp. 31–35 (1968).
Balog et al., Stud.Univ.Babes–Bolyai.Ser.Chem., vol. 14, No. 2, pp. 137–143 (1969).
Claremon et al., Tetrahedron Letters, vol. 29, No. 18, pp. 2155–2158 (1988).
Jones et al., Tetrahedron Letters, vol. 29, No. 31, pp. 3853–3856 (1988).
Imoto et al., Bull.Chem.Soc.Japan, vol. 59, pp. 3207–3212 (1986).
Hanzlik et al., Biochimica et Biophysica Acta, vol. 1035, pp. 62–70 (1990).
Liu et al., Biochimica et Biophysica Acta, vol. 1158, pp. 264–272 (1993).
Pickin et al., Biochemical Soc.Transactions, vol. 18, p. 316 (1990).
Thompson et al., J.Med.Chem., vol. 29, pp. 104–111 (1986).
Dufour et al., Biochemistry, vol. 34, No. 28, pp. 9136–9143 (1995).
Brisson et al., J.Biol.Chem., vol. 261, No. 20, pp. 9087–9089 (1986).
Khalid et al., Drugs Exptl.Clin.Res., Suppl. 1, XIII, pp. 57–60 (1987).
Liang et al., Arch. Biochemistry and Biophysics, vol. 252, No. 2, pp. 626–634 (1987).
Asboth et al., Biochemistry, vol. 24, pp. 606–609 (1985).
Irikura et al., Chemical Abstract, 68:30062 and Derwent Abstract, 66–20058F [00], (JP) 67010206—Jun. 1, 1967.
Irikura et al., Chemical Abstract, 70:37502 and Derwent Abstract, 66–32185F [00], (JP) 68010619—May 4, 1968.
Irikura et al., Chemical Abstract , 67:64704 and Derwent Abstract, 66–26788F [00], (JP) 67009133—May 6, 1967.
Irikura et al., Chemical Abstract, 73:45853 and Derwent Abstract, 70–37948R [21], (JP) 70015013 B—May 27, 1970.
Yoshida et al., Chemical Abstract, 110:213341 and Derwent Abstract, 89–028224 [04], (JP) 63301868—12/81988.
Leplawy et al., Chemical Abstract, 90:152624, patent PL–93135—May 30, 1977.
North et al., Tetrahedron, vol. 46, No. 24, pp. 8267–8290 (1990).
Harada et al., Institution of Molecular and Cellular Evolution, pp. 157–168 (1972).

* cited by examiner

DIPEPTIDE NITRILE CATHEPSIN K INHIBITORS

This invention relates to inhibitors of cysteine proteases, in particular to dipeptide nitrile cathepsin K inhibitors and to their pharmaceutical use for the treatment or prophylaxis of diseases or medical conditions in which cathepsin K is implicated.

Cathepsin K is a member of the family of lysosomal cysteine cathepsin enzymes, e.g. cathepsins B, K, L and S, which are implicated in various disorders including inflammation, rheumatoid arthritis, osteoarthritis, osteoporosis, tumors (especially tumor invasion and tumor metastasis), coronary disease, atherosclerosis (including atherosclerotic plaque rupture and destabilization), autoimmune diseases, respiratory diseases, infectious diseases and immunologically mediated diseases (including transplant rejection).

Our copending International patent application WO 99/24460 describes dipeptide nitriles which are inhibitors of cysteine cathepsins and their use for treatment of cysteine cathepsin dependent diseases or medical conditions. New dipeptide nitrile compounds have now been made which are inhibitors of cathepsin K, and which have desirable properties for pharmaceutical applications.

Accordingly the present invention provides a compound of formula I, or a pharmaceutically acceptable salt or ester thereof:

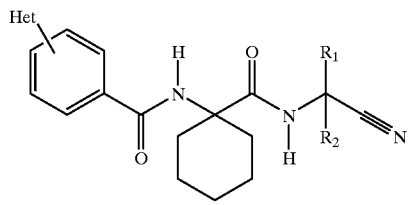

In which
  $R_1$ and $R_2$ are independently H or $C_1$–$C_7$lower alkyl, or $R_1$ and $R_2$ together with the carbon atom to which they are attached form a $C_3$–$C_8$cycloalkyl ring, and
  Het is an optionally substituted nitrogen-containing heterocyclic substituent, provided that Het is not 4-pyrrol-1-yl.

The Het substituent may be at the 2- or 3-position of the phenyl ring, though is preferably at the 4-position.

In the present description "nitrogen-containing heterocycle" signifies a heterocyclic ring system containing at least one nitrogen atom, from 2 to 10, preferably from 3 to 7, most preferably 4 or 5, carbon atoms and optionally one or more additional heteroatoms selected from O, S or preferably N.

Het may comprise an unsaturated, e.g. an aromatic, nitrogen-containing heterocycle; though preferably comprises a saturated nitrogen-containing heterocycle. Particularly preferred saturated nitrogen-containing heterocycles are piperazinyl, preferably piperazin-1-yl, or piperidinyl, preferably piperidin-4-yl.

Het may be substituted by one or more substituents, e.g. by up to 5 substituents independently selected from halogen, hydroxy, amino, nitro, optionally substituted $C_{1-4}$alkyl (e.g. alkyl substituted by hydroxy, alkyloxy, amino, optionally substituted alkylamino, optionally substituted dialkylamino, aryl or heterocyclyl), $C_{1-4}$alkoxy.

Preferably Het is substituted at a nitrogen atom, most preferably mono-substituted at a nitrogen atom.

Preferred substituents for Het are $C_1$–$C_7$lower alkyl, $C_1$–$C_7$lower alkoxy-$C_1$–$C_7$lower alkyl, $C_5$–$C_{10}$aryl-$C_1$–$C_7$lower alkyl, or $C_3$–$C_8$cycloalkyl.

$R_1$ and $R_2$ as $C_1$–$C_7$lower alkyl are preferably the same, e.g. methyl, or $R_1$ and $R_2$ together with the carbon atom to which they are attached preferably form a $C_3$–$C_8$cycloalkyl ring, e.g. a cyclopropyl ring. Most preferably both $R_1$ and $R_2$ are H.

Thus in particularly preferred embodiments the invention provides a compound of formula II, or a pharmaceutically acceptable salt or ester thereof:

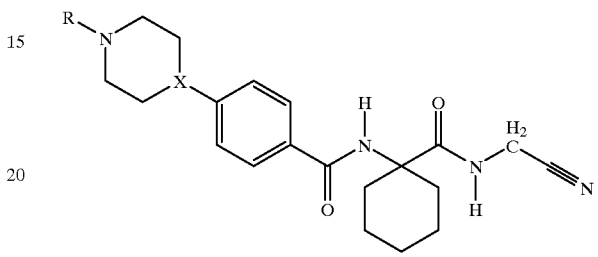

wherein X is CH or N, and
  R is H, $C_1$–$C_7$lower alkyl, $C_1$–$C_7$lower alkoxy-$C_1$–$C_7$lower alkyl, $C_5$–$C_{10}$aryl-$C_1$–$C_7$lower alkyl, or $C_3$–$C_8$cycloalkyl.

Thus particular examples of R as $C_1$–$C_7$lower alkyl are methyl, ethyl, n-propyl, or i-propyl.

A particular example of R as $C_1$–$C_7$lower alkoxy-$C_1$–$C_7$lower alkyl is methoxyethyl.

A particular example of R as $C_5$–$C_{10}$aryl-$C_1$–$C_7$lower alkyl is benzyl.

A particular example of R as $C_3$–$C_8$cycloalkyl is cyclopentyl.

Examples of particular compounds of formula II are:

N-[1-(Cyanomethyl-carbamoyl)-cyclohexyl]-4-(piperazin-1-yl)-benzamide;
N-[1-(Cyanomethyl-carbamoyl)-cyclohexyl]-4-(4-methyl-piperazin-1-yl)-benzamide;
N-[1-(Cyanomethyl-carbamoyl)-cyclohexyl]-4-(4-ethyl-piperazin-1-yl)-benzamide;
N-[1-(Cyanomethyl-carbamoyl)-cyclohexyl]-4-[4-(1-propyl)-piperazin-1-yl]-benzamide;
N-[1-(Cyanomethyl-carbamoyl)-cyclohexyl]-4-(4-isopropyl-piperazin-1-yl)-benzamide;
N-[1-(Cyanomethyl-carbamoyl)-cyclohexyl]-4-(4-benzyl-piperazin-1-yl)-benzamide;
N-[1-(Cyanomethyl-carbamoyl)-cyclohexyl]-4-[4-(2-methoxy-ethyl)-piperazin-1-yl]-benzamide;
N-[1-(Cyanomethyl-carbamoyl)-cyclohexyl]-4-(1-propyl-piperidin-4-yl)-benzamide;
N-[1-(Cyanomethyl-carbamoyl)-cyclohexyl]-4-[1-(2-methoxy-ethyl)-piperidin-4-yl]-benzamide;
N-[1-(Cyanomethyl-carbamoyl)-cyclohexyl](1-isopropyl-piperidin-4-yl)-benzamide;
N-[1-(Cyanomethyl-carbamoyl)-cyclohexyl]-4-(1-cyclopentyl-piperidin-4-yl)-benzamide;
N-[1-(Cyanomethyl-carbamoyl)-cyclohexyl]-4-(1-methyl-piperidin-4-yl)-benzamide, and
N-[1-(Cyanomethyl-carbamoyl)-cyclohexyl]-4-(piperidin-4-yl)-benzamide.

Compounds of formula I and II and the specific compounds above are hereinafter referred to as Compounds of the Invention.

Compounds of the Invention may be prepared by coupling the corresponding Het substituted benzoic acid derivative with 1-amino-cyclohexanecarboxylic acid cyanomethyl amide. For example, the benzoic acid derivative, preferably in the form of its hydrochloride, is mixed with 1-amino-cyclohexanecarboxylic acid cyanomethyl amide, e.g. in the presence of HOBT (1-hydroxybenzotriazole), WSCD and trimethylamine, in solution, e.g. in DMF, and stirred, e.g. overnight at room temperature. The product may be recovered, for instance, by evaporation of the solvent, followed by washing with aqueous sodium carbonate solution, preferably under mildly basic conditions, followed by solvent extraction, e.g. with ethyl acetate, drying of the extract, e.g. over sodium sulfate, evaporation of the solvent and filtration. Alternative procedures and reagents may be used; for instance, as hereinafter described in the Examples.

Thus in a further aspect the invention provides a process for the preparation of a compound of formula I which comprises coupling the corresponding Het substituted benzoic acid derivative of formula III:

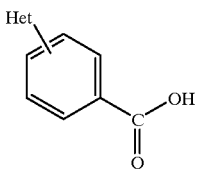

III

With 1-amino-cyclohexanecarboxylic acid cyanomethylamide.

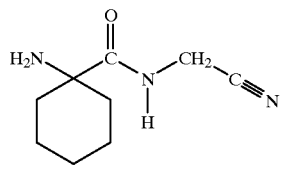

1-Amino-cyclohexanecarboxylic acid cyanomethylamide may be prepared by coupling 1-amino-cyclohexane carboxylic acid, typically in appropriate amino protected form, e.g. FMOC-1-amino-cyclohexane carboxylic acid, with 2-aminoacetonitrile. For example, FMOC-1-amino-cyclohexane carboxylic acid, e.g. with HOBT and WSCD, is added to a solution of 2-aminoacetonitrile and triethylamine in DMF and the mixture stirred at 25° C. overnight. 1-Amino-cyclohexanecarboxylic acid cyanomethyl-amide may be recovered as described in the Examples. FMOC-1-aminocyclohexane carboxylic acid may be prepared as described in the Examples.

Compounds of the invention are either obtained in the free form, or as a salt thereof if salt forming groups are present.

Compounds of the Invention having basic groups can be converted into acid addition salts, especially pharmaceutically acceptable salts. These are formed, for example, with inorganic acids, such as mineral acids, for example sulfuric acid, a phosphoric or hydrohalic acid, or with organic carboxylic acids, such as ($C_1$–$C_4$)alkanecarboxylic acids which, for example, are unsubstituted or substituted by halogen, for example acetic acid, such as saturated or unsaturated dicarboxylic acids, for example oxalic, succinic, maleic or fumaric acid, such as hydroxycarboxylic acids, for example glycolic, lactic, malic, tartaric or citric acid, such as amino acids, for example aspartic or glutamic acid, or with organic sulfonic acids, such as ($C_1$–$C_4$)-alkylsulfonic acids (for example methanesulfonic acid) or arylsulfonic acids which are unsubstituted or substituted (for example by halogen). Preferred are salts formed with hydrochloric acid, methanesulfonic acid and maleic acid.

In view of the close relationship between the free compounds and the compounds in the form of their salts, whenever a compound is referred to in this context, a corresponding salt is also intended, provided such is possible or appropriate under the circumstances.

The compounds, including their salts, can also be obtained in the form of their hydrates, or include other solvents used for their crystallization.

The compounds of the invention exhibit valuable pharmacological properties in mammals and are particularly useful as inhibitors of cathepsin K.

The cathepsin K inhibitory effects of the compound of the invention can be demonstrated in vitro by measuring the inhibition of e.g. recombinant human cathepsin K.

The in vitro assay is carried out as follows:

For cathepsin K:

The assay is performed in 96 well microtiter plates at ambient temperature using recombinant human cathepsin K. Inhibition of cathepsin K is assayed at a constant enzyme (0.16 nM) and substrate concentration (54 mM Z-Phe-Arg-AMCA-Peptide Institute Inc. Osaka, Japan) in 100 mM sodium phosphate buffer, pH 7.0, containing 2 mM dithiothreitol, 20 mM Tween 80 and 1 mM EDTA. Cathepsin K is preincubated with the inhibitors for 30 min, and the reaction is initiated by the addition of substrate. After 30 min incubation the reaction is stopped by the addition of E-64 (2 mM), and fluorescence intensity is read on a multi-well plate reader at excitation and emission wavelengths of 360 and 460 nm, respectively. Compounds of the Invention typically have Kis for human cathepsin K of less than about 50 nM, preferably of about 5 nM or less, e.g. about 1 nM.

In view of their activity as inhibitors of cathepsin K, Compounds of the Invention are particularly useful in mammals as agents for treatment and prophylaxis of diseases and medical conditions involving elevated levels of cathepsin K. Such diseases include diseases involving infection by organisms such as *pneumocystis carinii, trypsanoma cruzi, trypsanoma brucei, crithidia fusiculata,* as well as parasitic diseases such as schistosomiasis and malaria, tumours (tumour invasion and tumour metastasis), and other diseases such as metachromatic leukodystrophy, muscular dystrophy, amytrophy and similar diseases.

Cathepsin K, has been implicated in diseases of excessive bone loss, and thus the Compounds of the Invention may be used for treatment and prophylaxis of such diseases, including osteoporosis, gingival diseases such as gingivitis and periodontitis, Paget's disease, hypercalcemia of malignancy, e.g. tumour-induced hypercalcemia and metabolic bone disease. Also the Compounds of the Invention may be use for treatment or prophylaxis of diseases of excessive cartilage or matrix degradation, including osteoarthritis and rheumatoid arthritis as well as certain neoplastic diseases involving expression of high levels of proteolytic enzymes and matrix degradation.

Compounds of the Invention, are also indicated for preventing or treating coronary disease, atherosclerosis (including atherosclerotic plaque rupture and destabilization), autoimmune diseases, respiratory diseases and immunologically mediated diseases (including transplant rejection).

Compounds of the Invention are particularly indicated for preventing or treating osteoporosis of various genesis (e.g. juvenile, menopausal, post-menopausal, post-traumatic, caused by old age or by cortico-steroid therapy or inactivity).

Beneficial effects are evaluated in in vitro and in vivo pharmacological tests generally known in the art, and as illustrated herein.

The above cited properties are demonstrable in in vitro and in vivo tests, using advantageously mammals, e.g. rats, mice, dogs, rabbits, monkeys or isolated organs and tissues, as well as mammalian enzyme preparations, either natural or prepared by e.g. recombinant technology. Compounds of the Invention can be applied in vitro in the form of solutions, e.g. preferably aqueous solutions or suspensions, and in vivo either enterally or parenterally, advantageously orally, e.g. as a suspension or in aqueous solution, or as a solid capsule or tablet formulation. The dosage in vitro may range between about $10^{-5}$ molar and $10^{-9}$ molar concentrations. The dosage in vivo may range, depending on the route of administration, between about 0.1 and 100 mg/kg.

In accordance with the present invention it has been found that Compounds of the Invention, have good bioavailability, in particular good oral bioavailability. Thus, for example selected compounds of the Invention have absolute oral bioavailabilities of 50% or greater e.g. about 80% or more.

The antiarthritic efficacy of the Compounds of the Invention for the treatment of rheumatoid arthritis can be determined using models such as or similar to the rat model of adjuvant arthritis, as described previously (R. E. Esser, et. al. J. Rheumatology, 1993, 20, 1176.)

The efficacy of the compounds of the invention for the treatment of osteoarthritis can be determined using models such as or similar to the rabbit partial lateral meniscectomy model, as described previously (Colombo et al. Arth. Rheum. 1993 26, 875–886). The efficacy of the compounds in the model can be quantified using histological scoring methods, as described previously (O'Byrne et al. Inflamm Res 1995, 44, S117–S118).

The efficacy of the compounds of the invention for the treatment of osteoporosis can be determined using an animal model such as the ovariectomised rat or other similar species, e.g. rabbit or monkey, in which test compounds are administered to the animal and the presence of markers of bone resorption are measured in urine or serum (e.g. as described in Osteoporos Int (1997) 7:539–543).

Accordingly in further aspects the invention provides:

A Compound of the Invention for use as a pharmaceutical;

a pharmaceutical composition comprising a Compound of the Invention as an active ingredient;

a method of treating a patient suffering from or susceptible to a disease or medical condition in which cathepsin K is implicated, comprising administering an effective amount of a Compound of the Invention to the patient, and the use of a Compound of the Invention for the preparation of a medicament for therapeutic or prophylactic treatment of a disease or medical condition in which cathepsin K is implicated.

The present invention relates to methods of using Compounds of the Invention and their pharmaceutically acceptable salts, or pharmaceutical compositions thereof, in mammals for inhibiting cathepsin K, and for the treatment of cathepsin K dependent conditions, such as the cathepsin K dependent conditions, described herein, e.g. inflammation, osteoporosis, rheumatoid arthritis and osteoarthritis.

Particularly the present invention relates to a method of selectively inhibiting cathepsin K activity in a mammal which comprises administering to a mammal in need thereof an effective cathepsin K inhibiting amount of a Compound of the Invention.

More specifically such relates to a method of treating osteoporosis, rheumatoid arthritis, osteoarthritis, and inflammation (and other diseases as identified above) in mammals comprises administering to a mammal in need thereof a correspondingly effective amount of a Compound of the Invention.

The following examples are intended to illustrate the invention and are not to be construed as being limitations thereon. Temperatures are given in degrees Centigrade. If not mentioned otherwise, all evaporations are performed under reduced pressure, preferably between about 15 and 100 mm Hg (=20–133 mbar). The structure of final products, intermediates and starting materials is confirmed by standard analytical methods, e.g. microanalysis and spectroscopic characteristics (e.g. MS, IR, NMR). Abbreviations used are those conventional in the art.

EXAMPLES

Synthesis of 1-Amino-cyclohexanecarboxylic acid cyanomethyl-amide

A. FMOC-1-aminocyclohexane carboxylic acid

The title compound is prepared from 1-aminocyclohexane carboxylic acid (700 mmol), FMOC-chloride (770 mmol), Diisopropyl-ethylamine (770 mmol) and 770 ml NaOH 1N in 950 ml dioxan by conventional methods. Mp. 180–182° C.; Rf=0.21 (CH2Cl2/MeOH=95:5)

Acetonitrile may be used as solvent in place of dioxan.

B. FMOC-1-Amino-cyclohexanecarboxylic acid cyanomethyl-amide

2-Aminoacetonitrile hydrochloride (564 mmol) and triethylamine (564 mmol) are dissolved in DMF (1700 ml). FMOC-1-aminocyclohexane carboxylic acid (564 mmol), HOBt (564 mmol) and WSCD (564 mmol) are added and the mixture is stirred at 25° C. overnight. After evaporation of the solvent, the residue is dissolved in a mixture of water and sodium carbonate (to ensure slightly basic conditions) and extracted three times with ethyl acetate. The extract is washed with water, 10% citric acid, brine, sodium bicarbonate, brine and dried over magnesium sulfate and evaporated. The residue is suspended in diethylether and the solid filtered of and dried (vacuum). A white powder with mp. 167–169° C., Rf=0.27 (n-hexane:ethyl acetate=1:1) is obtained.

Alternatively TBF may be used as the solvent and 1-chloro-3,5-dimethoxytriazine (CDMT) as the activator, together with N-methylmorpholine (NMM) during the coupling reaction; in which case the product may be recovered by addition of isopropylacetate and water, separation of the organic phase followed by washing with brine, partial evaporation of the solvent, recovery of the crystallised product by filtration and drying.

C. 1-Amino-cyclohexanecarboxylic acid cyanomethyl-amide

FMOC-1-amino-cyclohexanecarboxylic acid cyanomethyl-amide (248 mmol) is dissolved in DMF (200 ml), piperidine (248 mmol) is added and the mixture is stirred at RT for 2 hours. The reaction mixture is poured into water (3000 ml) and stirred for 30 minutes. The suspension is filtered and the filtrate is acidified with HCl 4N and than extracted with ethyl acetate. NaOH 1N is added to make the water phase basic and the mixture is extracted three times with ethyl acetate. The organic fractions are dried over sodium sulfate and the solvent is evaporated. The residue is dried (vacuum) to yield a pale yellow oil. Rf=0.26 (CH2Cl2/MeOH=95:5).

1H-NMR (d6-DMSO): 1.05–1.80 (m, 10 H); 4.0 (br. s, 2H); NH very broad signal.

Alternatively THF may be used in place of DMF and diethylamine inplace of piperidine in the the FMOC deprotection step.

Example 1

Synthesis of N-[1-(Cyanomethyl-carbamoyl)-cyclohexyl]-4-piperazin-1-yl-benzamide

A. 4-piperazin-1-yl-benzoic acid methyl ester 1-(4–Cyanophenyl)-piperazine (11 mmol) is dissolved in 15 ml of a mixture of concentrated sulfonic acid and methanol (5N) and stirred in a sealed tube at 110° C. for 3 hours. After evaporation of the solvent, the residue is dissolved in water and extracted with ethyl acetate. Addition of sodium carbonate to the water phase until pH=9 results in the precipitation of a white solid which is filtered off and dried (vacuum). A white powder with Rf=0.59 ($CH_2Cl_2$/MeOH (+$NH_3$ 3N)=9:1) is obtained.

B. 4-piperazin-1-yl-benzoic acid hydrochlorid 4-piperazin-1-yl-benzoic acid methyl ester (17 mmol) is dissolved in 6N HCl (25 ml) and heated under reflux for 3 hours. The mixture is cooled in an ice bath to 0–4° C. and the solid material formed is filtered off, washed with acetone and dried (vacuum). A white powder with mp. >240° C. is obtained.

C. 4-(4-FMOC-piperazin-1-yl)-benzoic acid

4-Piperazin-1-yl-benzoic acid hydrochlorid (10.5 mmol) is dissolved in 15 ml Dioxan and 11.6 ml NaOH (2N) and cooled to 0° C. Simultaneously, FMOC-chloride (11.6 mmol) in dioxan (5 ml) and diisopropyl-ethylamine (11.6 mmol) in dioxan (5 ml) are added dropwise over 20 minutes at 0° C. and the mixture is stirred for 15 minutes and is then allowed to warm up to rt and is stirred over night. The mixture is diluted with water (50 ml) and extracted 2 times with diethylether. The water phase is acidified with aqueous HCl (4N) at 0–4° C. and the solid material formed is filtered off, washed with water and dried (vacuum). A white powder with Rf=0.2 ($CH_2Cl_2$/MeOH =95:5) is obtained.

D. N-[1-(Cyanomethyl-carbamoyl)-cyclohexyl]-4-(4-FMOC-piperazin-1-yl)-benzamide 1-Amino-cyclohexanecarboxylic acid cyanomethylamide (8.3 mmol) 4-(4-FMOC-piperazin-1-yl)-benzoic acid (8.3 mmol), HOBT (8.3 mmol) and WSCD (8.3 mmol) are dissolved in DMF (20 ml) and stirred overnight at rt. After evaporation of the solvent, the residue is dissolved in a mixture of water and sodium carbonate (to ensure slightly basic conditions) and extracted three times with ethyl acetate. The combined extract is dried over sodium sulfate and evaporated. The residue is purified by flash chromatography on silica gel with (ethylacetate/hexane=4:1) as mobile phase. The product containing fractions are combined and evaporated. The residue is suspended in diethylether and the solid filtered of and dried (vacuum). A white powder with mp. 192–194° C., Rf=0.26 ($CH_2Cl_2$/MeOH=95:5) is obtained.

E. N-[1-(Cyanomethyl-carbamoyl)-cyclohexyl]-4-(piperazin-1-yl)-benzamide

N-[1-(Cyanomethyl-carbamoyl)-cyclohexyl]-4-(4-FMOC-piperazin-1-yl)-benzamide (4.4 mmol) is dissolved in DMF (15 ml), piperidine (4.4 mmol) is added and the mixture is stirred at RT for 4 hours. 4 additional drops of piperidine are added and the mixture is stirred over night. The reaction mixture is poured into water and ethyl acetate and the suspension is filtered and the filtrate is acidified with HCl 4N and then extracted with ethyl acetate. Saturated sodium carbonate solution is added to make the water phase basic and the mixture is extracted three times with ethyl acetate. The water phase is saturated with sodium chloride and extracted three times with ethyl acetate again. The organic fractions are dried over sodium sulfate and the solvent is evaporated. The residue is purified by flash chromatography on silica gel with $CH_2Cl_2$/MeOH (with 3N NH3)=95:5 as mobile phase. The product containing fractions are combined and evaporated. The residue is suspended in diethylether and the solid filtered of and dried (vacuum). A white powder with mp. 206–210° C., Rf=0.28 ($CH_2Cl_2$/MeOH (with 3N $NH_3$)=9:1) is obtained.

1H-NMR (d6-DMSO): 1.15–1.35 (m, 1H); 1.4–1.6 (m, 5H); 1.65–1.8 (m, 2H); 2.05–2.15 (m, 2H); 2.8 (m, 4H); 3.15 (m, 4H); 4.0 (d, 2H), 6.95 (d, 2H); 7.65 (s, 1H); 7.75 (d, 2H), 8.15 (m, 1H).

Example 2

Synthesis of N-[1-(Cyanomethyl-carbamoyl)-cyclohexyl]-4-(4-methyl-piperazin-1-yl)-benzamide

A. 4-(4-Methyl-piperazin-1-yl)-benzoic acid methyl ester

4-Fluorobenzoic acid methyl ester (34 mmol), 1-methyl-piperazine (75 mmol) and potassium carbonate (34 mmol) are suspended in acetonitrile (30 ml) and stirred under reflux for three days. After evaporation of the solvent, the residue is dissolved in water and extracted three times with ethyl acetate. The extract is dried over sodium sulfate and evaporated. The residue is purified by flash chromatography on silica gel with ($CH_2Cl_2$/MeOH=95:5) as mobile phase. The product containing fractions are combined and evaporated. The residue is suspended in diethylether/pentane and the solid filtered of and dried (vacuum). A pale yellow powder with mp. 117–119° C., Rf=0.20 ($CH_2Cl_2$/MeOH=95:5) is obtained.

B. 4-(4-Methyl-piperazin-1-yl)-benzoic acid hydrochlorid 4-(4-Methyl-piperazin-1-yl)-benzoic acid methyl ester (8.5 mmol) is dissolved in 4N HCl (15 ml) and heated under reflux for 8 hours. The mixture is cooled in an ice bath to 0–4° C., diluted with 5 ml acetone and the solid material formed is filtered off, washed with acetone and dried (vacuum). A white powder with mp. >270° C., Rf=0.11 ($CH_2Cl_2$/MeOH=9:1) is obtained.

C. N-[1-(Cyanomethyl-carbamoyl)-cyclohexyl]-4-(4-methyl-piperazin-1-yl)-benzamide 1-Amino-cyclohexanecarboxylic acid cyanomethylamide (1.38 mmol) 4-(4-methyl-piperazin-1-yl)-benzoic acid hydrochloride (1.38 mmol), HOBT (1.38 mmol), WSCD (1.38 mmol) and triethylamine (1.38 mmol) are dissolved in DMF (5 ml) and stirred overnight at rt. After evaporation of the solvent, the residue is dissolved in a mixture of water and sodium carbonate (to ensure slightly basic conditions) and extracted three times with ethyl acetate. The combined extract is dried over sodium sulfate and evaporated. The residue is suspended in diethylether and the solid filtered of and dried (vacuum). A pale powder with mp. 218–220° C., Rf=0.19 (CH$_2$Cl$_2$/MeOH=9:1) is obtained.

1H-NMR (d6-DMSO): 1.15–1.35 (m, 1H); 1.4–1.6 (m, 5H); 1.65–1.8 (m, 2H); 2.05–2.15 (m, 2H); 2.2 (s, 3H); 2.4 (m, 4H); 3.2 (m, 4H); 4.0 (d, 2H), 6.95 (d, 2H); 7.65 (s 1H); 7.75 (d, 2H), 8.15 (m, 1H).

Example 3

Synthesis of N-[1-(Cyanomethyl-carbamoyl)-cyclohexyl]-4-(4-ethyl-piperazin-1-yl)-benzamide

A. 4-(4-Ethyl-piperazin-1-yl)-benzoic acid methyl ester

4-Fluorobenzoic acid methyl ester (53 mmol), 1-ethyl-piperazine (44 mmol) and potassium carbonate (44 mmol) are suspended in dimethyl-acetamide (50 ml) and stirred under reflux overnight. After evaporation of the solvent, the residue is dissolved in water and extracted three times with ethyl acetate. The extract is dried over sodium sulfate and evaporated. The residue is suspended in diethylether/pentane and the solid filtered of and dried (vacuum). A brownish powder with mp. 102–104° C., Rf=0.22 (CH$_2$Cl$_2$MeOH=95:5) is obtained.

B. 4-(4-Ethyl-piperazin-1-yl)-benzoic acid hydrochlorid 4-(4-Ethyl-piperazin-1-yl)-benzoic acid methyl ester (15 mmol) is dissolved in 4N HCl (35 ml) and heated under reflux for 8 hours. The mixture is cooled in an ice bath to 0–4° C. and the solid material formed is filtered off, washed with acetone and dried (vacuum). A grey powder with mp. >270° C., Rf=0.08 (CH$_2$Cl$_2$/MeOH=9:1) is obtained.

C. N-[1-(Cyanomethyl-carbamoyl)-cyclohexyl]-4-(4-ethyl-piperazin-1-yl)-benzamide 1-Amino-cyclohexanecarboxylic acid cyanomethyl-amide (0.9 mmol) 4-(4-ethyl-piperazin-1-yl)-benzoic acid hydrochloride (0.9 mmol), HOBT (0.9 mmol), WSCD (0.9 mmol) and triethylamine (0.9 mmol) are dissolved in DMF (5 ml) and stirred overnight at rt. After evaporation of the solvent, the residue is dissolved in a mixture of water and sodium carbonate (to ensure slightly basic conditions) and extracted three times with ethyl acetate. The combined extract is dried over sodium sulfate and evaporated. The residue is purified by flash chromatography on silica gel with CH$_2$Cl$_2$/MeOH (with 3N NH$_3$)=93:7 as mobile phase. The product containing fractions are combined and evaporated. The residue is suspended in diethylether and the solid filtered of and dried (vacuum). A white powder is obtained.

1H-NMR (d6-DMSO): 1.0 (t, 3H), 1.15–1.35 (m, 1H); 1.4–1.6 (m, 5H); 1.65–1.8 (m, 2H); 2.05–2.15 (m, 2H); 2.35 (q, 2H); 2.45 (m, 4H); 3.2 (m, 4H); 4.0 (d, 2H), 6.95 (d, 2H); 7.65 (s, 1H); 7.75 (d, 2H), 8.15 (m, 1H).

Example 4

Synthesis of N-[1-(Cyanomethyl-carbamoyl)-cyclohexyl]-4-[4-(1-propyl)-piperazin-1-yl]-benzamide

A. 4-[4-(1-Propyl)-piperazin-1-yl]-benzoic acid methyl ester

4-Fluorobenzoic acid methyl ester (165 mmol), 1-(1-propyl)-piperazine dihydrobromide (138 mmol) and potassium carbonate (690 mmol) are suspended in dimethylacetamide (320 ml) and stirred under reflux overnight. After evaporation of the solvent, the residue is dissolved in water and extracted three times with ethyl acetate. The extract is dried over sodium sulfate and evaporated. The residue is suspended in diethylether/pentane and the solid filtered of and dried (vacuum). A brownish powder with mp. 99–101° C., Rf=0.23 (CH$_2$Cl$_2$/MeOH=95:5) is obtained.

Cs$_2$CO$_3$ may be used in place of K$_2$CO$_3$ in the above procedure.

B. 4-[4-(1-Propyl)-piperazin-1-yl]-benzoic acid hydrochlorid

4-[4-(1-Propyl)-piperazin-1-yl]-benzoic acid methyl ester (38 mmol) is dissolved in 4N HCl (60 ml) and heated under reflux for 7 hours. The mixture is cooled in an ice bath to 0–4° C. and the solid material formed is filtered off, washed with cold water and dried (vacuum). A pale powder with mp. >270° C., Rf=0.19 (CH2Cl2/MeOH=9:1) is obtained.

Alternatively the 4-[4-(1-Propyl)-piperazin-1-yl]-benzoic acid product may be produced as an internal salt with acetic acid. For instance, the 4-[4-(1-Propyl)-piperazin-1-yl]-benzoic acid methyl ester is suspended in water/methanol at 70° and hydrolysed by addition of 1 equivalent of NaOH; the solution is clearfiltered and the product precipitated by addition of 1 equivalent of acetic acid, filtered and dried.

C. N-[1-(Cyanomethyl-carbamoyl)-cyclohexyl]-4-[4-(1-propyl)-piperazin-1-yl]-benzamide 1-Amino-cyclohexanecarboxylic acid cyanomethyl-amide (22 mmol), 4-[4-(1-propyl)-piperazin-1-yl]-benzoic acid hydrochloride (22 mmol), HOBT (22 mmol), WSCD (22 mmol) and triethylamine (22 mmol) are dissolved in DMF (50 ml) and stirred overnight at rt. After evaporation of the solvent, the residue is dissolved in a mixture of water and sodium carbonate (to ensure slightly basic conditions) and extracted three times with ethyl acetate. The combined extract is dried over sodium sulfate and evaporated. The residue is purified by flash chromatography on silica gel with (CH$_2$Cl$_2$/MeOH=9:1) as mobile phase. The product containing fractions are combined and evaporated. The residue is suspended in diethylether and the solid filtered of and dried (vacuum). A white powder with mp. 216–218° C., Rf=0.34 (CH$_2$Cl$_2$/MeOH=9:1) is obtained.

1H-NMR (d6-DMSO): 0.85 (t, 3H), 1.2–1.3 (m, 1H); 1.4–1.6 (m, 7H); 1.65–1.8 (m, 2H); 2.05–2.15 (m, 2H); 2.25 (t, 2H); 2.45 (m, 4H); 3.2 (m, 4H); 4.0 (d, 2H), 6.95 (d, 2H); 7.65 (s, 1H); 7.75 (d, 2H), 8.15 (m, 1H).

In an alternative procedure the acetic acid internal salt of 4-[4-(1-propyl)-piperazin-1-yl]-benzoic acid is treated in acetonitrile with HOBt, NMM and diisopropylcarbodiimide (DICI), and after stirring for 1 hr at 40° C. a solution of 1-amino-cyclohexanecarboxylic acid cyanomethyl-amide in acetonitrile is added. On completion of the reaction, the product is precipitated by addition of water to the reaction mixture, filtered and following digestion with ethanol is dried to the end product.

Example 5

Synthesis of N-[1-(Cyanomethyl-carbamoyl)-cyclohexyl]-4-(4-isopropyl-piperazin-1-yl)-benzamide

A. 4-[4-Isopropyl-piperazin-1-yl]-benzoic acid methyl ester

Tris-(dibenzylidene-acetone)-dipalladium (0.05 mmol), (2'-dicyclohexylphosphanyl-biphenyl-2-yl)-dimethyl-amine (0.1 mmol) and potassium carbonate (4.6 mmol) are suspended in 1,2-dimethoxyethane (10 ml) in an oxygen-free atmosphere (N2). 4-Bromo-benzoic acid methyl ester (3.3 mmol) and 1-isopropyl-piperazine (3.9 mmol) are added and the stirred mixture is heated under reflux for 28 hours. After cooling the solvent is evaporated and water is added to the residue, which is then extracted three times with ethyl acetate. The combined extract is dried over sodium sulfate and evaporated. The residue is purified by flash chromatography on silica gel with ($CH_2Cl_2$/MeOH=95:5) as mobile phase. The product containing fractions are combined and evaporated. The residue is suspended in diethylether/pentane and the solid filtered of and dried (vacuum). A pale-brown powder with Rf=0.23 ($CH_2Cl_2$/MeOH=95:5) is obtained.

B. 4-(4-Isopropyl-piperazin-1-yl)-benzoic acid hydrochloride 4-(4-Isopropyl-piperazin-1-yl)-benzoic acid methyl ester (0.9 mmol) is dissolved in 4N HCl (2 ml) and heated under reflux for 7 hours. The mixture is cooled in an ice bath to 0–4° C. and acetone is added. The solid material formed is filtered off, washed with cold acetone and dried (vacuum). A pale-brown powder with mp. >270° C., Rf=0.08 ($CH_2Cl_2$/MeOH=9:1) is obtained.

C. N-[1-(Cyanomethyl-carbamoyl)-cyclohexyl]-4-(4-isopropyl-piperazin-1-yl)-benzamide 1-Amino-cyclohexanecarboxylic acid cyanomethyl-amide (0.6 mmol), 4-(4-isopropyl-piperazin-1-yl)-benzoic acid hydrochloride (0.6 mmol), HOBT (0.6 mmol), WSCD (0.6 mmol) and triethylamine (0.6 mmol) are dissolved in DMF (2 ml) and stirred overnight at rt. After evaporation of the solvent, the residue is dissolved in a mixture of water and sodium carbonate (to ensure slightly basic conditions) and extracted three times with ethyl acetate. The combined extract is dried over sodium sulfate and evaporated. The residue is suspended in ethyl acetate/diethylether and the solid filtered of and dried (vacuum). A white powder with mp. 218–220° C., Rf=0.28 ($CH_2Cl_2$/MeOH=9:1) is obtained.

1H-NMR (d6-DMSO): 1.0 (d, 6H), 1.2–1.3 (m, 1H); 1.4–1.6 (m, 5H); 1.65–1.8 (m, 2H); 2.05–2.15 (m, 2H); 2.45 (m, 4H); 2.65 (m, 1H); 3.2 (m, 4H); 4.0 (d, 2H); 6.95 (d, 2H); 7.65 (s, 1H); 7.75 (d, 2H), 8.15 (m, 1H).

Example 6

Synthesis of N-[1-(Cyanomethyl-carbamoyl)-cyclohexyl]-4-(4-benzyl-piperazin-1-yl)-benzamide

A. 4-(4-Benzyl-piperazin-1-yl)-benzoic acid methyl ester

Tris-(dibenzylidene-acetone)-dipalladium (0.03 mmol), (2'-dicyclohexylphosphanyl-biphenyl-2-yl)-dimethyl-amine (0.9 mmol) and NaOtBu (6.5 mmol) are suspended in toluene (20 ml) in an oxygen-free atmosphere (N2). 4-Bromo-benzoic acid methyl ester (4.65 mmol) and 1-(benzyl)-piperazine (5.6 mmol) are added and the stirred mixture is heated under reflux for 4 hours. After cooling, a mixture of ethylacetate and diethylether is added and the mixture is filtered. Then the solvent is evaporated and the residue is suspended in diethylether and the solid filtered of and dried (vacuum). A pale powder with mp. 105–107° C., Rf=0.67 ($CH_2Cl_2$/MeOH=95:5) is obtained.

B. 4-(4-Benzyl-piperazin-1-yl)-benzoic acid hydrochloride 4-(4-Benzyl-piperazin-1-yl)-benzoic acid methyl ester (0.84 mmol) is dissolved in 4N HCl (2 ml) and heated under reflux for 8 hours. The mixture is cooled in an ice bath to 0–4° C. and the solid material formed is filtered off, washed with cold acetone and dried (vacuum). A grey powder with mp. >270° C., Rf=0.18 ($CH_2Cl_2$/MeOH=95:5) is obtained.

C. N-[1-(Cyanomethyl-carbamoyl)-cyclohexyl]-4-(4-benzyl-piperazin-1-yl)-benzamide 1-Amino-cyclohexanecarboxylic acid cyanomethyl-amide (0.84 mmol), 4-[4-(2-propyl)-piperazin-1-yl]-benzoic acid hydrochloride (0.84 mmol), HOBT (0.84 mmol), WSCD (0.84 mmol) and triethylamine (0.84 mmol) are dissolved in DMF (2 ml) and stirred overnight at rt. After evaporation of the solvent, the residue is dissolved in a mixture of water and sodium carbonate (to ensure slightly basic conditions) and extracted three times with ethyl acetate. The combined extract is dried over sodium sulfate and evaporated. The residue is suspended in methanol and the solid filtered of and dried (vacuum). A pale powder with mp. 210–212° C., Rf=0.20 ($CH_2Cl_2$/MeOH=95:5) is obtained.

1H-NMR (d6-DMSO): 1.15–1.35 (m, 1H); 1.4–1.6 (m, 5H); 1.65–1.8 (m, 2H); 2.05–2.15 (m, 2H); 2.45 (m, 4H); 3.2 (m, 4H); 3.5 (s, 2H); 4.0 (d, 2H), 6.9 (d, 2H); 7.2–7.4 (m, 5H), 7.65 (s, 1H); 7.75 (d, 2H), 8.15 (m, 1H).

Example 7

Synthesis of N-[1-(Cyanomethyl-carbamoyl)-cyclohexyl]-4-[4-(2-methoxy-ethyl)-piperazin-1-yl]-benzamide

A. 4-(4-Benzyl-piperazin-1-yl)-benzoic acid methyl ester

4-Fluorobenzoic acid methyl ester (200 mmol), 1-benzyl-piperazine (300 mmol), and potassium carbonate (300 mmol) are suspended in acetonitrile (400 ml) and stirred under reflux for 6 days. After evaporation of the solvent, the residue is dissolved in water and extracted three times with diethylether. The extract is dried over sodium sulfate and evaporated. The residue is purified by flash chromatographic on silica gel with ($CH_2Cl_2$ first, then $CH_2Cl_2$/MeOH=15:1) as mobile phase. The product containing fractions are combined and evaporated. The residue is suspended in diethylether/pentane and the solid filtered of and dried (vacuum). A powder with mp. 105–107° C. is obtained.

B. 4-(Piperazin-1-yl)-benzoic acid methyl ester 4-(4-Benzyl-piperazin-1-yl)-benzoic acid methyl ester (19.4 mmol) is dissolved in methanol (150 ml) and Pd/charcoal is added (0.6 g). The mixture is stirred in a hydrogen atmosphere until consumption has ceased. The catalyst is filtered off and the filtrate evaporated. The residue is suspended in diethylether/pentane and the solid filtered of and dried (vacuum). A powder with mp. 95–97° C. is obtained.

C. [4-(2-methoxy-ethyl)-piperazin-1-yl]-benzoic acid methyl ester 4-(Piperazin-1-yl)-benzoic acid methyl ester (19 mmol), 2-bromoethylmethylether (21 mmol), and potassium carbonate (22.8 mmol) are suspended in acetonitrile (50 ml) and stirred at 80° C. for 8 hours. After evaporation of the solvent, the residue is dissolved in water and extracted three times with $CH_2Cl_2$. The extract is dried over sodium sulfate and evaporated. The residue is suspended in diethylether/ pentane and the solid filtered of and dried (vacuum). A powder with mp. 103–105° C. is obtained.

D. [4-(2-methoxy-ethyl)-piperazin-1-yl]-benzoic acid hydrochloride

[4-(2-methoxy-ethyl)-piperazin-1-yl]-benzoic acid methyl ester (17 mmol) is dissolved in 4N HCl (70 ml) and heated under reflux for 5 hours. After cooling the solvent is evaporated and the residue is suspended in ethanol and the solid filtered of, washed with diethylether and dried (vacuum). A powder with mp. >270° C., Rf=0.35 ($CH_2Cl_2$/MeOH=9:1) is obtained.

E. N-[1-(Cyanomethyl-carbamoyl)-cyclohexyl]-4-[4-(2-methoxy-ethyl)-piperazin-1-yl]-benzamide 1-Amino-cyclohexanecarboxylic acid cyanomethylamide (1.0 mmol), [4-(2-methoxy-ethyl)-piperazin-1-yl]-benzoic acid hydrochloride (1.0 mmol), HOBT (1.0 mmol), WSCD (1.0 mmol) and triethylamine (1.0 mmol) are dissolved in DMF (4 ml) and stirred overnight at rt. After evaporation of the solvent, the residue is dissolved in a mixture of water and sodium carbonate (to ensure slightly basic conditions) and extracted three times with ethyl acetate. The combined extract is dried over sodium sulfate and evaporated. The residue is purified by flash chromatography on silica gel with $CH_2Cl_2$/MeOH=92.5:7.5 as mobile phase. The product containing fractions are combined and evaporated. The residue is suspended in diethylether and the solid filtered of and dried (vacuum). A pale powder with mp. 166–168° C., Rf=0.37 ($CH_2Cl_2$/MeOH=9:1) is obtained.

1H-NMR (d6-DMSO): 1.15–1.35 (m, 1H); 1.4–1.6 (m, 5H); 1.65–1.8 (m, 2H); 2.05–2.15 (m, 2H); 2.45 (m, 6H); 3.2 (m, 7H); 3.45 (t, 2H); 4.0 (d, 2H), 6.95 (d, 2H); 7.65 (s, 1H); 7.75 (d, 2H), 8.15 (m, 1H).

Example 8

Synthesis of N-[1-(Cyanomethyl-carbamoyl)-cyclohexyl]-4-(1-propyl-piperidin-4-yl)-benzamide

A. 1-(4-Phenyl-piperidin-1-yl)-ethanone

4-Phenylpiperidine (87 mmol) and pyridine (96 mmol) are dissolved in dry $CH_2Cl_2$ (100 ml) and acetylchloride (96 mmol) in $CH_2Cl_2$ (40 ml) is added dropwise to the stirred solution at 10° C. The reaction is stirred for 1 hour at rt. The mixture is extracted three times with water and the water phase is extracted again with $CH_2Cl_2$. The combined organic phases are dried over sodium sulfate and evaporated. A pale brown oil with Rf=0.13 (ethyl acetate/hexane=1:1) is obtained.

B. 4-Piperidin-4-yl-benzoic acid 1-(4-Phenyl-piperidin-1-yl)-ethanone (84 mmol) is dissolved in $CH_2Cl_2$ (250 ml) and oxalylchloride (336 mmol) is added dropwise at −20 to −10° C. After the oxalylchloride addition aluminium trichloride (260 mmol) is added in portions at −10° C. The mixture is stirred at −10° C. for 3 hours. The cooling bath is removed and the mixture is stirred at rt overnight. The mixture is poured on ice/water (600 ml) and extracted 3 times with $CH_2Cl_2$. The combined organic phases are washed with water, dried over sodium sulfate and evaporated. The residue is dissolved in aqueous sodium hydroxide solution (2N, 250 ml) and 6N HCl is added at 0° C. to acidify the solution. The precipitate formed is filtered off and washed with water. The solid material is suspended in 6N HCl (300 ml) and the mixture is heated for 18 hours under reflux. After cooling to rt the solvent is removed and the residue is suspended in ethanol. The solid material is filtered of and dried. A brown powder with mp. >270° C. is obtained.

C. 4-Piperidin-4-yl-benzoic acid methyl ester

4-Piperidin-4-yl-benzoic acid (47 mmol) is dissolved in methanol (300 ml) and 1 ml of concentrated sulfonic acid is added. The mixture is heated under reflux overnight. After evaporation of the solvent, the residue is dissolved in a mixture of water and sodium carbonate (to ensure basic conditions) and extracted three times with ethyl acetate. The combined extract is dried over sodium sulfate and evaporated. A brown powder with Rf=0.18 ($CH_2Cl_2$/MeOH=9:1) is obtained.

D. 4-(1-Propyl-piperadin-4-yl)-benzoic acid methyl ester

4-Piperidin-4-yl-benzoic acid methyl ester (28 mmol), ethyldiisopropylamine (31 mol) and 1-iodopropane (42 mmol) are dissolved in 1,2-dimethoxyethane (100 ml) and the mixture is heated at 70° C. overnight. After evaporation of the solvent, the residue is dissolved in a mixture of water and sodium carbonate (to ensure basic conditions) and extracted three times with ethyl acetate. The combined extract is dried over sodium sulfate and evaporated. The residue is purified by flash chromatography on silica gel with $CH_2Cl_2$/MeOH=9:1 as mobile phase. The product containing fractions are combined and evaporated. The residue is suspended in diethylether and the solid filtered of and dried (vacuum). A pale brown powder with Rf=0.35 ($CH_2Cl_2$/MeOH=9:1) is obtained.

E. 4-(1-Propyl-piperidin-4-yl)-benzoic acid hydrochloride 4-(1-Propyl-piperidin-4-yl)-benzoic acid methyl ester (32 mmol) is dissolved in 4N HCl (45 ml) and heated under reflux for 7 hours. The mixture is cooled in an ice bath to 0–4° C. and the solid material formed is filtered off, washed with cold acetone and dried (vacuum). A brown powder with mp. >270° C., Rf=0.08 ($CH_2Cl_2$/MeOH=9:1) is obtained.

F. N-[1-(Cyanomethyl-carbamoyl)-cyclohexyl]-4-(1-propyl-piperidin-4-yl)-benzamide 1-Amino-cyclohexanecarboxylic acid cyanomethylamide (23 mmol), 4-(1-propyl-piperidin-4-yl)-benzoic acid hydrochloride (23 mmol), HOBT (23 mmol), WSCD (23 mmol) and triethylamine (23 mmol) are dissolved in DMF (50 ml) and stirred overnight at rt. After evaporation of the solvent, the residue is dissolved in a mixture of water and sodium carbonate (to ensure basic conditions) and extracted three times with ethyl acetate. The combined extract is dried over sodium sulfate and evaporated. The residue is suspended in diethylether/pentane and the solid filtered of and dried (vacuum). A pale powder with mp. 198–200° C., Rf=0.34 ($CH_2Cl_2$/MeOH=9:1) is obtained.

1H-NMR (d6-DMSO): 0.85 (t, 3H); 1.2–1.3 (m, 1H); 1.4–1.6 (m, 7H); 1.6–1.8 (m, 6H); 1.9–2.0 (m, 2H); 2.05–2.15 (m, 2H); 2.25 (t, 2H); 2.55 (m, 1H); 2.95 (d, 2H); 4.0 (d, 2H), 7.35 (d, 2H); 7.8 (d, 2H), 7.9 (s, 1H); 8.15 (m, 1H).

Example 9

Synthesis of N-[1-(Cyanomethyl-carbamoyl)-cyclohexyl]-4-[1-(2-methoxy-ethyl)-piperidin-4-yl]-benzamide

A. 4-Carboxybenzeneboronic acid methyl ester

4–Carboxybenzeneboronic acid (300 mmol) is dissolved in methanol (400 ml) and 1.5 ml concentrated HCl is added to the stirred solution. The reaction is heated under reflux for 30 hours. The solvent is evaporated, the remaining residue is suspended in diethylether and the solid filtered of and dried (vacuum). A pale powder with mp. 201–205° C., Rf=0.28 (CH$_2$Cl$_2$/MeOH=95:5) is obtained. This powder is a mixture of 4-carboxybenzeneboronic acid methyl ester and the dimeric anhydride of 4-carboxybenzeneboronic acid methyl ester and is used without further purification.

B. 4-Pyridin-4-yl-benzoic acid methyl ester

4-Carboxybenzeneboronic acid methyl ester (248 mmol) from A, 4-bromopyridine (248 mmol), tetrakis-(triphenylphosphin)-palladium (2.5 mmol) and potassium carbonate (744 mmol) are suspended in 1,2-dimethoxyethane (1100 ml). The stirred mixture is heated under reflux for 8 hours. After cooling the solvent is evaporated and water is added to the residue which is then extracted three times with ethyl acetate. The combined extract is dried over sodium sulfate and evaporated. The residue is suspended in diethylether and the solid filtered of and dried (vacuum). A pale-brown powder with mp. 99–101° C., Rf=0.39 (CH$_2$Cl$_2$/MeOH=95:5) is obtained.

C. 4-(4-Methoxycarbonyl-phenyl)-1-(2-methoxy-ethyl)-pyridinium; bromide

4-Pyridin-4-yl-benzoic acid methyl ester (70 mmol) and 2-bromoethyl-methylether (28 ml) are heated for 1 hour to 110° C. After cooling the reaction mixture is suspended in acetone and the solid filtered of and dried (vacuum). A pale-brown powder with mp. 170–171° C., Rf=0.22 (CH$_2$Cl$_2$/MeOH=9:1) is obtained.

D. 4-[1-(2-Methoxy-ethyl)-piperidin-4-yl]-benzoic acid methyl ester 4-(4-Methoxycarbonyl-phenyl)-1-(2-methoxy-ethyl)-pyridinium; bromide (67 mmol) is suspended in methanol (250 ml) and platinoxide (1.2 g) is added. The mixture is stirred in a hydrogen atmosphere at normal pressure until consumption has ceased. The catalyst is filtered off and the filtrate evaporated. The residue is dissolved in CH$_2$Cl$_2$ and extracted with aqueous sodium carbonate solution. The organic phase is dried over sodium sulfate and evaporated. The residue is purified by flash chromatography on silica gel with CH$_2$Cl$_2$/MeOH=9:1 as mobile phase. The product containing fractions are combined and evaporated. A pale yellow oil with Rf=0.22 (CH$_2$Cl$_2$/MeOH=95:5) is obtained.

E. 4-[1-(2-Methoxy-ethyl)-piperidin-4-yl]-benzoic acid hydrochloride

4-[1-(2-Methoxy-ethyl)-piperidin-4-yl]-benzoic acid methyl ester (47 mmol) is dissolved in 4N HCl (80 ml) and heated under reflux for 12 hours. After cooling the solvent is evaporated and the residue is suspended in acetone and the solid filtered of, washed with acetone and dried (vacuum). A white powder with mp. >270° C. is obtained.

F. N-[1-(Cyanomethyl-carbamoyl)-cyclohexyl]-4-[1-(2-methoxy-ethyl)-piperidin-4-yl]-benzamide 1-Amino-cyclohexanecarboxylic acid cyanomethyl-amide (107 mmol), 4-[1-(2-methoxy-ethyl)-piperidin-4-yl]-benzoic acid hydrochloride (107 mmol), HOBT (107 mmol), WSCD (107 mmol) and triethylamine (107 mmol) are dissolved in DMF (250 ml) and stirred overnight at rt. After evaporation of the solvent, the residue is dissolved in a mixture of water and sodium carbonate (to ensure slightly basic conditions) and extracted three times with ethyl acetate. The combined extract is dried over sodium sulfate and evaporated. The residue is purified by flash chromatography on silica gel with CH$_2$Cl$_2$/MeOH (with 2N NH$_3$)=9:1 as mobile phase. The product containing fractions are combined and evaporated. The residue is suspended in diethylether/ethyl acetate and the solid filtered of and dried (vacuum). A pale powder with mp. 160–162° C., Rf=0.42 (CH$_2$Cl$_2$/MeOH (with 3N NH$_3$)=9:1) is obtained.

1H-NMR (d6-DMSO): 1.2–1.3 (m, 1H); 1.4–1.6 (m, 5H); 1.6–1.8 (m, 6H); 2.0–2.2 (m, 4H); 2.45 (m, 2H); 2.55 (m, 1H); 2.95 (br. d, 2H); 3.2 (s, 3H); 3.4 (dd, 2H); 4.0 (d, 2H); 7.35 (d, 2H); 7.8 (d, 2H); 7.9 (s, 1H); 8.15 (m, 1H).

Example 10

N-[1-(Cyanomethyl-carbamoyl)-cyclohexyl]-4-(1-isopropyl-piperidin-4-yl)-benzamide

A. 1-Isopropyl-4-(4-methoxycarbonyl-phenyl)-pyridinium; bromide

4-Pyridin-4-yl-benzoic acid methyl ester (2.3 mmol) and 2-iodopropane (1.0 ml) are heated for 24 hours to 90° C. After cooling the solvent is evaporated and the residue is suspended in acetone and the solid filtered of and dried (vacuum). A pale-yellow powder with mp. 187–189° C., Rf=0.27 (CH$_2$Cl$_2$/MeOH=9:1) is obtained.

B. 4-(1-Isopropyl-piperidin-4-yl)-benzoic acid methyl ester hydroiodide

1-Isopropyl-4-(4-methoxycarbonyl-phenyl)-pyridinium; bromide (1.9 mmol) is suspended in methanol (10 ml) and platinoxide (80 mg) is added. The mixture is stirred in a hydrogen atmosphere at normal pressure until consumption has ceased. The catalyst is filtered off and the filtrate evaporated. The residue is suspended in diethylether/pentane and the solid filtered of and dried (vacuum). A pale powder with mp. 219–224° C., Rf=0.41 (CH$_2$Cl$_2$/MeOH=9:1) is obtained.

C. 4-(1-Isopropyl-piperidin-4-yl)-benzoic acid hydrochloride 4-(1-Isopropyl-piperidin-4-yl)-benzoic acid methyl ester hydroiodide (1.7 mmol) is dissolved in 4N HCl (5 ml) and heated under reflux for 10 hours. After cooling the solvent is evaporated and the residue is suspended in acetone and the solid filtered of, washed with acetone and dried (vacuum). A grey-brown powder with mp. >270° C. is obtained.

D. N-[1-(Cyanomethyl-carbamoyl)-cyclohexyl-4-(1-isopropyl-piperidin-4-yl)-benzamide 1-Amino-cyclohexanecarboxylic acid cyanomethyl-amide (0.95 mmol), 4-(1-isopropyl-piperidin-4-yl)-benzoic acid hydrochloride (0.95 mmol), HOBT (0.95 mmol), WSCD (0.95 mmol) and triethylamine (0.95 mmol) are dissolved in DMF (5 ml) and stirred overnight at rt. After evaporation of the solvent, the residue is dissolved in a mixture of water and sodium carbonate (to ensure basic conditions) and extracted three times with ethyl acetate. The combined extract is dried over sodium sulfate and evaporated. The residue is suspended in diethylether and the solid filtered of and dried (vacuum). A white powder with mp. 214–216° C., Rf=0.38 (CH$_2$Cl$_2$/MeOH (with 3N NH$_3$)=9:1) is obtained.

1H-NMR (d6-DMSO): 0.95 (d, 6H); 1.2–1.3 (m, 1H); 1.4–1.8 (m, 11H); 2.05–2.25 (m, 4H); 2.55 (m, 1H); 2.7 (m,

1H); 2.85 (d, 2H); 4.0 (d, 2H); 7.35 (d, 2H); 7.8 (d, 2H), 7.9 (s, 1H); 8.15 (m, 1H).

Example 11

N-[1-(Cyanomethyl-carbamoyl)-cyclohexyl]-4-(1-cyclopentyl-piperidin-4-yl)-benzamide

A. 1–Cyclopentyl-4-(4-methoxycarbonyl-phenyl)-pyridinium; bromide

4-Pyridin-4-yl-benzoic acid methyl ester (2.35 mmol) and 1-iodocyclopentane (1.0 ml) are heated for 4 hours to 110° C. 1-Iodocyclopentane (0.5 ml) are added and the mixture is heated for another 4 hours to 120° C. After cooling the solvent is evaporated and the residue is suspended in acetone and the solid filtered of and dried (vacuum). The solid residue is purified by flash chromatography on silica gel with $CH_2Cl_2$/MeOH=9:1 as mobile phase. The product containing fractions are combined and evaporated. The residue is suspended in diethylether and the solid filtered of and dried (vacuum). A yellow powder with mp. 183–185° C., Rf=0.35 ($CH_2Cl_2$/MeOH=9:1) is obtained.

B. 4-(1–Cyclopentyl-piperidin-4-yl)-benzoic acid methyl ester hydroiodide

1-Cyclopentyl-4-(4-methoxycarbonyl-phenyl)-pyridinium; bromide (1.27 mmol) is suspended in methanol (8 ml) and platinoxide (50 mg) is added. The mixture is stirred in a hydrogen atmosphere at normal pressure until consumption has ceased. The catalyst is filtered off and the filtrate evaporated. The residue is suspended in diethylether/pentane and the solid filtered of and dried (vacuum). A pale powder with mp. 204–210° C., Rf=0.27 ($CH_2Cl_2$/MeOH=95:5) is obtained.

C. 4-(1–Cyclopentyl-piperidin-4-yl)-benzoic acid hydrochloride 4-(1–Cyclopentyl-piperidin-4-yl)-benzoic acid methyl ester hydroiodide (1.06 mmol) is dissolved in 4N HCl (5 ml) and heated under reflux for 10 hours. After cooling the solvent is evaporated and the residue is suspended in acetone and the solid filtered of, washed with acetone and dried (vacuum). A grey-brown powder with mp. >270° C. is obtained.

D. N-[1-(Cyanomethyl-carbamoyl)-cyclohexyl]-4-(1-cyclopentyl-piperidin-4-yl)-benzamide 1-Amino-cyclohexanecarboxylic acid cyanomethylamide (0.74 mmol), 4-(1-cyclopentyl-piperidin-4-yl)-benzoic acid hydrochloride (0.74 mmol), HOBT (0.74 mmol), WSCD (0.74 mmol) and triethylamine (0.74 mmol) are dissolved in DMF (5 ml) and stirred overnight at rt. After evaporation of the solvent, the residue is dissolved in a mixture of water and sodium carbonate (to ensure basic conditions) and extracted three times with ethyl acetate. The combined extract is dried over sodium sulfate and evaporated. The residue is suspended in diethylether and the solid filtered of and dried (vacuum). A white powder with mp. 233–234° C., Rf=0.34 ($CH_2Cl_2$/MeOH (with 3N $NH_3$)=9:1) is obtained.

1H-NMR (d6-DMSO): 1.2–1.85 (m, 20H); 1.9–2.15 (m, 4H); 2.4–2.6 (m, 2H); 3.05 (d, 2H); 4.0 (d, 2H); 7.35 (d, 2H); 7.8 (d, 2H), 7.9 (s, 1H); 8.15 (m, 1H).

Example 12

N-[1-(Cyanomethyl-carbamoyl)-cyclohexyl]-4-(1-methyl-piperidin-4-yl)-benzamide

A. 4-Phenyl-1-methyl-piperidine

4-Phenylpiperidine (12.4 mmol), paraformaldehyde (24.8 mmol) and tetraisopropoxy-titanium (12.4 mmol) are suspended in 1,2-dimethoxyethane (20 ml) and warmed to 60° C. for 30 minutes and stirred at rt for one additional hour. Sodium borohydride (12.4 mmol) is added in portions and the mixture is stirred at rt for 2 hours and at 60° C. for additional 3 hours. After cooling the solvent is evaporated and the residue is dissolved in a mixture of aqueous ammonia (60 ml) and ethyl acetate and filtered carefully. The mixture is extracted three times with ethyl acetate and the combined organic phases are dried over sodium sulfate and evaporated. A pale brown oil is obtained.

B. 4-(1-Methyl-piperidin-4-yl)-benzoic acid methyl ester

4-Phenyl-1-methyl-piperidine (9.9 mmol) is dissolved in $CH_2Cl_2$ (60 ml) and oxalylchloride (39.6 mmol) is added dropwise at −20 to −10° C. After the oxalylchloride addition aluminium trichloride (260 mmol) is added in portions at −10° C. The mixture is stirred at −10° C. for 1.5 hours. Then the cooling bath is removed and the mixture is stirred at rt for another 2 hours. The mixture is cooled again to −0° C. and methanol (30 ml) is added dropwise. After completion of the methanol addition the cooling bath is removed and the mixture is stirred at rt overnight. The reaction mixture is poured into a mixture of aqueous sodium carbonate (to ensure basic conditions) and ethyl acetate and the suspension is filtered carefully. The filtrate is extracted three times with ethyl acetate and the combined extract is dried over sodium sulfate and evaporated. The residue is purified by flash chromatography on silica gel with $CH_2Cl_2$/MeOH=9:1 as mobile phase. The product containing fractions are combined and evaporated. A pale yellow oil with Rf=0.29 ($CH_2Cl_2$/MeOH=9:1) is obtained.

C. 4-(1-Methyl-piperidin-4-yl)-benzoic acid hydrochloride 4-(1-Methyl-piperidin-4-yl)-benzoic acid methyl ester (4.55 mmol) is dissolved in 4N HCl (10 ml) and heated under reflux for 8 hours. After cooling the solvent is evaporated and the residue is suspended in acetone and the solid filtered of, washed with acetone and dried (vacuum). A pale-brown powder with mp. >270° C. is obtained.

D. N-[1-(Cyanomethyl-carbamoyl)-cyclohexyl]-4-(1-methyl-piperidin-4-yl)-benzamide 1-Amino-cyclohexanecarboxylic acid cyanomethylamide (0.98 mmol), 4-(1-methyl-piperidin4-yl)-benzoic acid hydrochloride (0.98 mmol), HOBT (0.98 mmol), WSCD (0.98 mmol) and triethylamine (0.98 mmol) are dissolved in DMF (5 ml) and stirred overnight at rt. After evaporation of the solvent, the residue is dissolved in a mixture of water and sodium carbonate (to ensure basic conditions) and extracted three times with ethyl acetate. The combined extract is dried over sodium sulfate and evaporated. The residue is suspended in diethylether/pentane and the solid filtered of and dried (vacuum). A white powder with mp. 215–217° C., Rf=0.32 ($CH_2Cl_2$/MeOH (with 3N $NH_3$)=9:1) is obtained.

1H-NMR (d6-DMSO): 1.2–1.3 (m, 1H); 1.4–1.8 (m, 11H); 1.85–2.0 (m, 2H); 2.05–2.2 (m, 5H); 2.55 (m, 1H); 2.95 (d, 2H); 4.0 (d, 2H); 7.35 (d, 2H); 7.8 (d, 2H), 7.9 (s, 1H); 8.15 (m, 1H).

Similarly N-[1-(cyanomethyl-carbamoyl)-cyclohexyl]-4-(piperidin-4-yl)-benzamide is obtained substantially as described above in Example 12; for instance by omitting Step A and starting the synthesis procedure at step B, using 4-phenylpiperidine as the starting material.

What is claimed is:

1. N-[1-(Cyanomethyl-carbamoyl)-cyclohexyl]-4-[4-(1-propyl)-piperazin-1-yl]-benzamide, or a pharmaceutically acceptable salt thereof.

2. A pharmaceutical composition comprising a compound according to claim 1 as an active ingredient.

3. A method of treating a mammal suffering from a disease or medical condition which involves elevated levels of cathepsin K, such disease or medical condition being selected from hypercalcemia of malignancy, excessive bone loss, excessive cartilage degradation and excessive matrix degradation, comprising administering to said mammal an effective cathepsin K inhibiting amount of a compound according to claim 1.

4. A process for the preparation of N-[1-(cyanomethyl-carbamoyl)-cyclohexyl]-4-[4-(1-propyl)-piperazin-1-yl]-benzamide or a salt thereof according to claim 1, which comprises coupling 4-[4-(1-propyl)-piperazin-1-yl]benzoic acid or a salt thereof with 1-amino-cyclohexanecarboxylic acid cyanomethyl-amide.

5. A method of treating osteoporosis in a mammal comprising administering to said mammal an effective amount of a compound according to claim 1.

6. A method of treating rheumatoid arthritis in a mammal comprising administering to said mammal an effective amount of a compound according to claim 1.

7. A method of treating osteoarthritis in a mammal comprising administering to said mammal an effective amount of a compound according to claim 1.

8. A method of treating gingival diseases in a mammal comprising administering to said mammal an effective amount of a compound according to claim 1.

9. A method of treating Paget's disease in a mammal comprising administering to said mammal an effective amount of a compound according to claim 1.

10. A method of treating hypercalcemia of malignancy in a mammal comprising administering to said mammal an effective amount of a compound according to claim 1.

11. A method of selectively inhibiting cathepsin K activity in a mammal with elevated levels of cathepsin K which comprises administering to a mammal in need thereof an effective cathepsin K inhibiting amount of a compound according to claim 1.

* * * * *

UNITED STATES PATENT AND TRADEMARK OFFICE
CERTIFICATE OF CORRECTION

PATENT NO.     : 6,642,239 B2
DATED          : November 4, 2003
INVENTOR(S)    : Martin Missbach It is certified that error appears in the above-identified patent and that said Letters Patent is hereby corrected as shown below:

<u>Title page,</u>
Item [74], should read:
-- *Attorney, Agent, or Firm* — Carol A. Loeschorn, Norbert Gruenfeld --

Signed and Sealed this

Eleventh Day of May, 2004

JON W. DUDAS
*Acting Director of the United States Patent and Trademark Office*